(12) United States Patent
Hwang et al.

(10) Patent No.: US 7,402,390 B2
(45) Date of Patent: Jul. 22, 2008

(54) METHOD OF ISOLATING NUCLEIC ACID USING MATERIAL POSITIVELY CHARGED AT FIRST PH AND CONTAINING AMINO GROUP AND CARBOXYL GROUP

(75) Inventors: Kyu-youn Hwang, Incheon-si (KR); Joon-ho Kim, Seongnam-si (KR); Chang-eun Yoo, Seoul (KR); Hun-joo Lee, Seoul (KR); Hee-kyun Lim, Suwon-si (KR); Sung-young Jeong, Yongin-si (KR); Jeo-young Shim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 159 days.

(21) Appl. No.: 11/317,949

(22) Filed: Dec. 23, 2005

(65) Prior Publication Data

US 2006/0154284 A1    Jul. 13, 2006

(30) Foreign Application Priority Data

Dec. 23, 2004   (KR) ...................... 10-2004-0111165

(51) Int. Cl.
*C12Q 1/68*   (2006.01)
*G01N 33/53*   (2006.01)
*C07H 21/00*   (2006.01)

(52) U.S. Cl. ............................. 435/6; 435/7.1; 435/7.2; 536/23.1

(58) Field of Classification Search ...................... 435/6, 435/7.1, 7.2; 536/23.1
See application file for complete search history.

(56) References Cited

U.S. PATENT DOCUMENTS 6,310,199 B1    10/2001    Smith et al.
2001/0018513 A1    8/2001    Baker ...................... 536/25.41

*Primary Examiner*—Jezia Riley
(74) *Attorney, Agent, or Firm*—Cantor Colburn LLP

(57) ABSTRACT

A method of isolating nucleic acid from a sample containing nucleic acid is provided. The method includes contacting the sample with a bifunctional material that contains an amino group and a carboxyl group and is positively charged at a first pH to allow binding of the nucleic acid to the bifunctional material; and extracting the nucleic acid at a second pH higher than the first pH from the complex.

10 Claims, 3 Drawing Sheets

METHOD OF ISOLATING NUCLEIC ACID USING MATERIAL POSITIVELY CHARGED AT FIRST PH AND CONTAINING AMINO GROUP AND CARBOXYL GROUP

CROSS-REFERENCE TO RELATED PATENT APPLICATION

This application claims the benefit of Korean Patent Application No. 10-2004-0111165, filed on Dec. 23, 2004, in the Korean Intellectual Property Office, the disclosure of which is incorporated herein in its entirety by reference.

BACKGROUND OF THE INVENTION

1. Field of the Invention

The present invention relates to a method of isolating nucleic acid using a material containing an amino group and a carboxyl group and which is positively charged at a first pH.

2. Description of the Related Art

Conventional methods of isolating nucleic acid using pH-dependent ion-exchange matrices include U.S. Patent Publication No. 2001-0018513, which discloses a method of isolating nucleic acid using a material having an ionizable group, wherein the ionizable group is positively charged at a first pH so that the material can bind with nucleic acid, and the material releases the bound nucleic acid at a second pH which is higher than the first pH. Examples of the material having an ionizable group include N-2-acetamido-2-aminoethanesulfonic acid (ACES), N-2-acetamido-2-imidodiacetic acid (ADA), N-trihydroxymethyl-methyl-2-aminoethanesulfonic acid (TES), trihydroxymethylaminoethane (Tris) and the like. Furthermore, U.S. Pat. No. 6,310,199 discloses a method of isolating nucleic acid using a pH-dependent ion-exchange matrix comprising a silica magnetic particle and a plurality of first ion exchange ligands. Each of the first ion exchange ligands contains an aromatic hydrocarbon ring, a spacer covalently attached to the aromatic hydrocarbon ring, and a linker comprising a linker alkyl chain covalently attached to the silica magnetic particle at a first end of the chain and covalently attached to the amino terminus of the spacer at a second end of the chain.

However, despite the prior art methods described above, there is still a demand for a material having an ionizable group that can bind with nucleic acid at a high rate, and can release the bound nucleic acid with high efficiency upon an increase of pH. Thus, the inventors of the present invention have searched for a material which can bind with a nucleic acid at a higher rate to adsorb the nucleic acid rapidly, and can release the bound nucleic acid with remarkably high efficiency upon an increase of pH, and found a bifunctional material containing both a carboxyl group and an amino group, thereby completing the invention.

SUMMARY OF THE INVENTION

The present invention provides a method of isolating nucleic acid rapidly with high efficiency using a material which binds with nucleic acid rapidly, and releases the bound nucleic acid with high efficiency upon an increase of pH. According to an aspect of the present invention, there is provided a method of isolating nucleic acid from a sample containing nucleic acid, the method comprising: contacting the sample with a bifunctional material that contains an amino group and a carboxyl group and is positively charged at a first pH to allow binding of nucleic acid to the bifunctional material to form a nucleic acid-bifunctional material complex; and extracting the bound nucleic acid at a second pH which is higher than the first pH from the complex, wherein the bifunctional material is represented by the following Formula 1 or Formula 2:

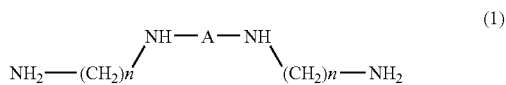

where n is an integer from 1 to 10; and A is

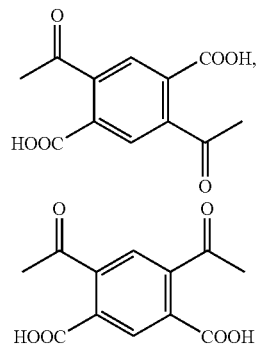

or a combination, from 1,2,4,5-benzenetetracarboxylic dianhydride;

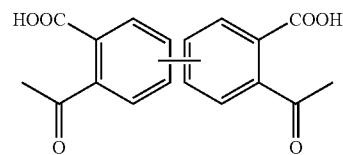

from 3,3',4,4'-biphenyltetracarboxylic dianhydride, 2,2',3,3'-biphenyltetracarboxylic dianhydride, or 2,3,3',4'-biphenyltetracarboxylic dianhydride;

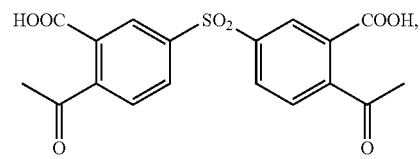

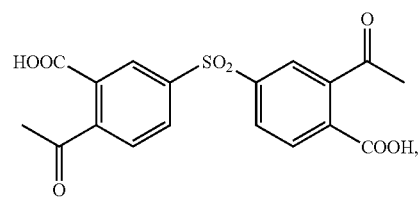

or a combination, from bis(3,4-dicarboxyphenyl)sulfone dianhydride;

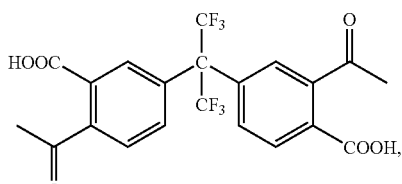
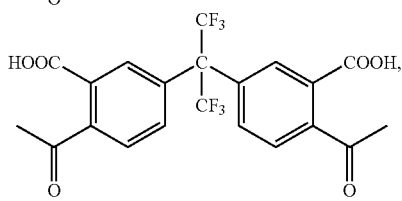

or a combination, from 2,2-bis(3,4-dicarboxyphenyl)-hexafluoropropane dianhydride;

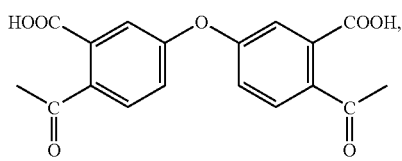
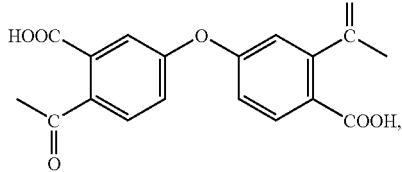

or a combination, from bis(3,4-dicarboxyphenyl) ether dianhydride;

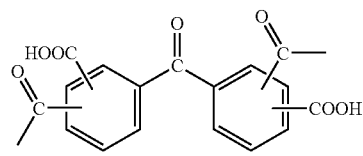

from 3,3',4,4'-benzophenonetetracarboxylic dianhydride, 2,2',3,3'-benzophenonetetracarboxylic dianhydride or 2,3,3',4'-benzophenonetetracarboxylic dianhydride;

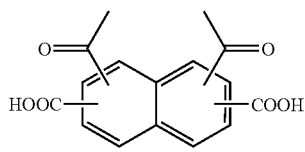

from 1,4,5,8-naphthalenetetracarboxylic dianhydride, 1,2,5,6-naphthalenetetracarboxylic dianhydride, or 2,3,6,7-naphthalenetetracarboxylic dianhydride, wherein the naphthalene is further unsubstituted or a carbonyl group and a carboxyl group is substituted on any carbon position except for a linking portion of the rings;

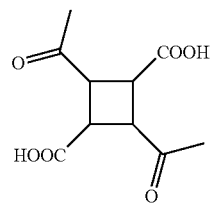

from cyclobutanetetracarboxylic dianhydride;

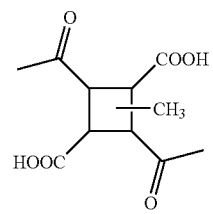

from methylcyclobutanetetracarboxylic dianhydride; or

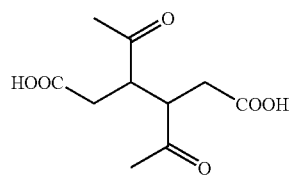

from 1,2,3,4-tetracarboxybutane dianhydride, wherein moiety A is a group generated from a reaction between the corresponding tetracarboxylic dianhydride, and an amino group of an $NH_2(CH_2)_nNH_2$ where n is an integer from 1 to 10; and

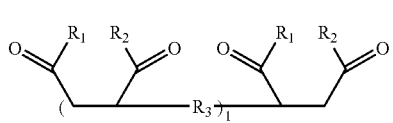

(2)

where $R_1$ and $R_2$ are each independently selected from the group consisting of an —OH group and an —$NH(CH_2)_nNH_2$ group, where n is an integer from 1 to 10; $R_3$ is an alkyl group having 1 to 10 carbon atoms; and l is an integer from 1 to 30,000.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
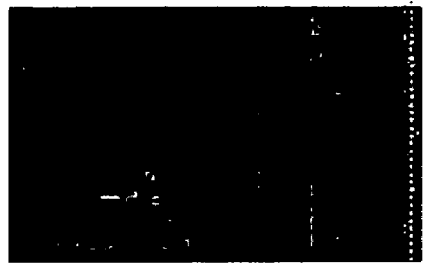
FIG. 1 is a diagram illustrating observations of the amounts of DNA bound at pH 3, 7 and 10, respectively.
Figure 1:
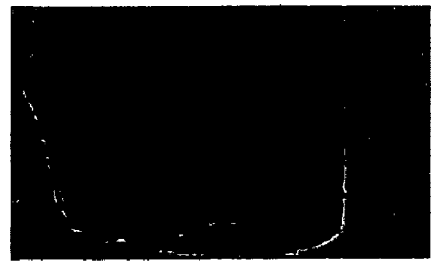
Figure 1:
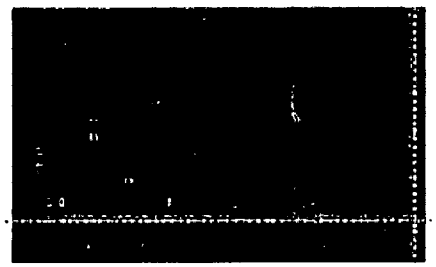
Figure 1:
Figure 1:
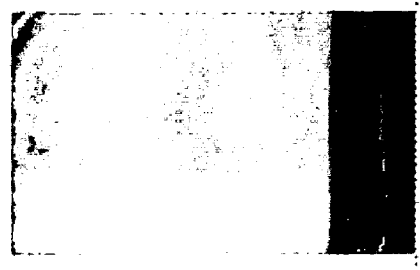
Figure 1:

A method of isolating nucleic acid from a sample containing nucleic acid according to an embodiment of the present invention includes: contacting the sample with a bifunctional material that contains an amino group and a carboxyl group and is positively charged at a first pH, to allow binding of nucleic acid to the bifunctional material; and extracting the bound nucleic acid at a second pH which is higher than the first pH.

The bifunctional material is represented by Formula 1 or Formula 2 below.

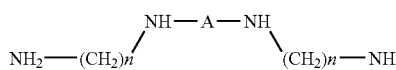
(1)

wherein n is an integer from 1 to 10; and A is

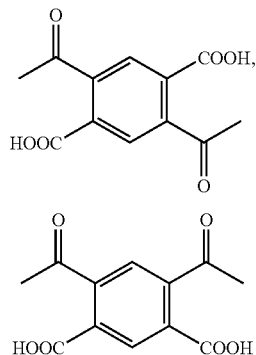

or a combination (from 1,2,4,5-benzenetetracarboxylic dianhydride),

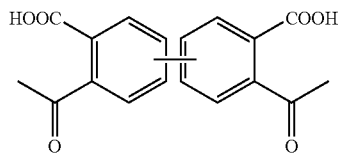

(from 3,3',4,4'-biphenyltetracarboxylic dianhydride, 2,2',3,3'-biphenyltetracarboxylic dianhydride, or 2,3,3',4'-biphenyltetracarboxylic dianhydride),

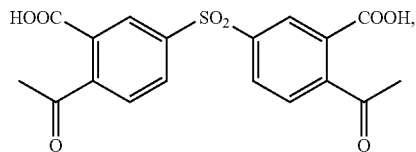

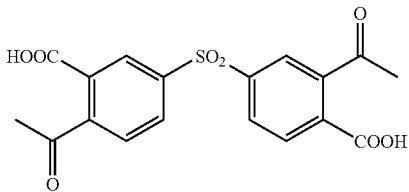

or a combination (from bis(3,4-dicarboxyphenyl)sulfone dianhydride),

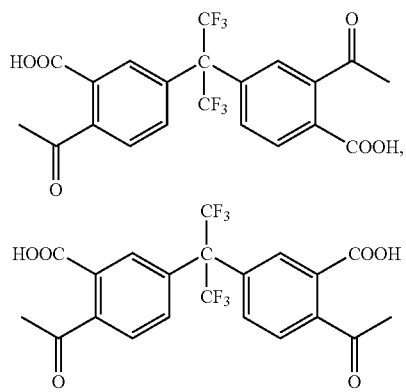

or a combination (from 2,2-bis(3,4-dicarboxyphenyl)-hexafluoropropane dianhydride),

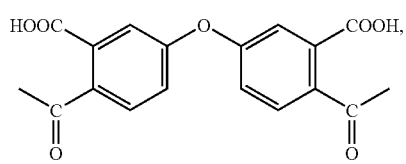

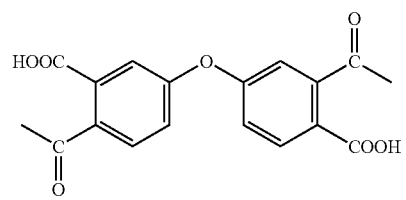

or a combination (from bis(3,4-dicarboxyphenyl) ether dianhydride),

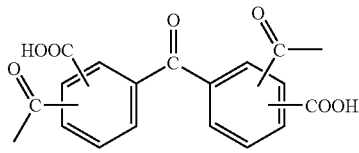

(from 3,3',4,4'-benzophenonetetracarboxylic dianhydride, 2,2',3,3'-benzophenonetetracarboxylic dianhydride, or 2,3,3', 4'-benzophenonetetracarboxylic dianhydride),

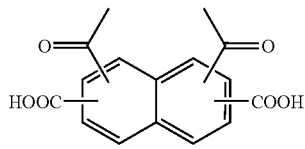

(from 1,4,5,8-naphthalenetetracarboxylic dianhydride, 1,2,5, 6-naphthalenetetracarboxylic dianhydride or 2,3,6,7-naphthalenetetracarboxylic dianhydride, wherein a carbonyl group and a carboxyl group may be substituted on any carbon position except for a linking portion of the rings),

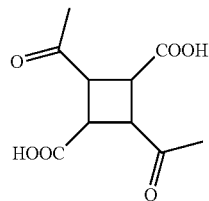

from cyclobutanetetracarboxylic dianhydride),

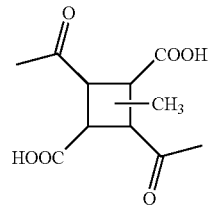

(from methylcyclobutanetetracarboxylic dianhydride), or

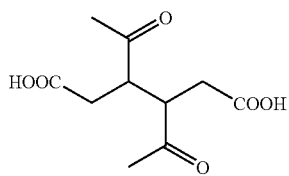

(1,2,3,4,-tetracarboxybutane dianhydride), wherein moiety A is a group generated by a reaction between the corresponding tetracarboxylic dianhydride (specified in parentheses), and an amino group of an $NH_2(CH_2)_nNH_2$ where n is an integer from 1 to 10; and

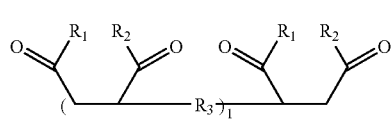

(2)

where $R_1$ and $R_2$ are each independently selected from the group consisting of an —OH group and an —$NH(CH_2)_nNH_2$ group where n is an integer from 1 to 10; $R_3$ is an alkyl group having 1 to 10 carbon atoms; and l is an integer from 1 to 30,000.

The method includes a process of bringing a sample into contact with a bifunctional material that contains an amino group and a carboxyl group and is positively charged at a first pH, to thus allow binding of nucleic acid to the bifunctional material. The sample contains nucleic acid and may be exemplified by a biological sample such as a solution containing blood and cells, or a chemical nucleic acid solution such as a solution containing a PCR product.

According to the present invention, the material to which the nucleic acid in the sample binds is a bifunctional material that contains an amino group and a carboxyl group and is positively charged at the first pH. Such a material may be a compound or a solid material in which such functional groups as described above are immobilized on a solid substrate. The solid substrate may be made of silicone, glass or plastic, but is not limited to these examples.

In an embodiment of the invention, the material is represented by Formula 3 or Formula 4 below.

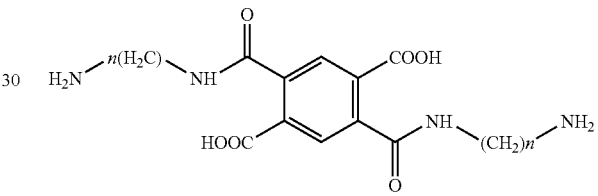

(3)

where n is an integer from 1 to 10.

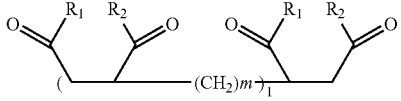

(4)

where $R_1$ and $R_2$ are each independently selected from the group consisting of an —OH group and an —$NH(CH_2)_nNH_2$ group where n is an integer from 1 to 10; m is an integer from 1 to 10; and l is an integer from 1 to 30,000.

The compounds of Formula 1 and Formula 2 are respectively compounds having an amino group and a carboxyl group. The compound of Formula 1 may have a positive charge to negative charge ratio of about 2:1 at a first pH, thus having a net positive charge of +1. More preferably, the compound of Formula 2 may be a compound of Formula 4 which contains the —OH group and the —$NH(CH_2)_nNH_2$ group at a ratio of about 2:1. An example of the compound of Formula 4 is a compound in which the —$NH(CH_2)_nNH_2$ group is an ethylenediamine group.

According to an embodiment of the present invention, the compound of Formula 1 can be obtained by chemically reacting a tetracarboxylic acid anhydride such as 1,2,4,5-benzenetetracarboxylic acid anhydride, with $NH_2(CH_2)_nNH_2$, where n is an integer from 1 to 10, such as ethylenediamine. Furthermore, the compound of Formula 2 can be obtained by chemically reacting the compound of Formula 5 below with $NH_2(CH_2)_nNH_2$, where n is an integer from 1 to 10. In the compound of Formula 2 resulting therefrom, the ratio of the —OH group and the —$NH(CH_2)_nNH_2$ group can be adjusted by controlling the concentration of $NH_2(CH_2)_nNH_2$ among the reactants.

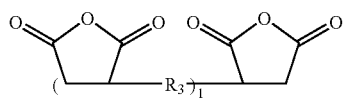

(5)

where $R_3$ is an alkyl group having 1 to 10 carbon atoms; and l is an integer from 1 to 30,000. The compound of Formula 5 may be the compound of Formula 6 below.

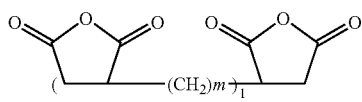

(6)

where m is an integer from 1 to 10; and l is an integer from 1 to 30,000.

The compound of Formula 5 is a polyanhydride polymer. This polymer can be easily separated from a solution through a separation process, such as centrifugation. Therefore, a nucleic acid-polymer complex which is obtained by allowing nucleic acid to bind the polymer of Formula 2 obtained from said polymer can be separated from its solution, and the nucleic acid can be easily separated from the complex with polymer by eluting the separated nucleic acid-polymer complex at a second pH.

In another embodiment of the present invention, the material is a solid phase material in which a group represented by Formula 7 or Formula 8 below is immobilized on a solid substrate:

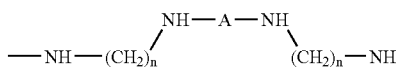

(7)

where n is an integer from 1 to 10; and and A is

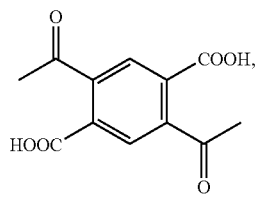

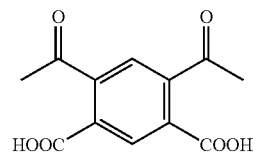

or a combination (from 1,2,4,5-benzenetetracarboxylic dianhydride),

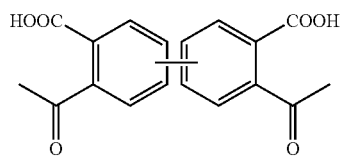

(from 3,3',4,4'-biphenyltetracarboxylic dianhydride, 2,2',3,3'-biphenyltetracarboxylic dianhydride, or 2,3,3',4'-biphenyltetracarboxylic dianhydride),

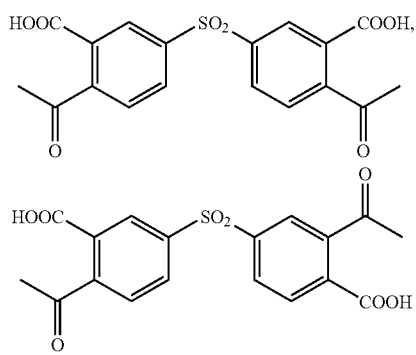

or a combination (from bis(3,4-dicarboxyphenyl)sulfone dianhydride),

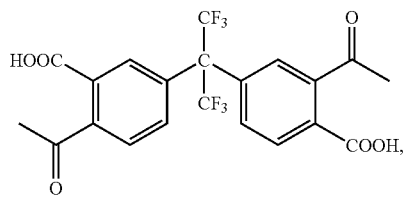

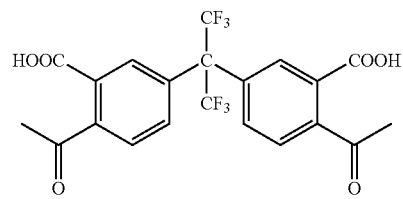

or a combination (from 2,2-bis(3,4-dicarboxyphenyl)-hexafluoropropane dianhydride),

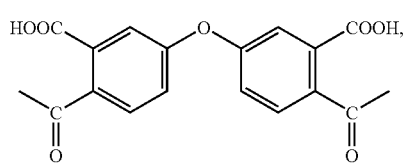

-continued

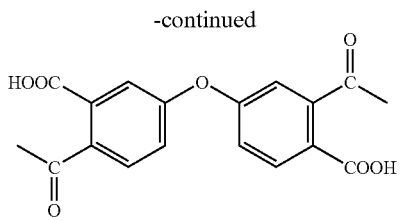

or a combination (from bis(3,4-dicarboxyphenyl) ether dianhydride),

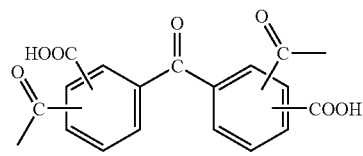

from 3,3',4,4'-benzophenonetetracarboxylic dianhydride, 2,2',3,3'-benzophenonetetracarboxylic dianhydride, or 2,3,3', 4'-benzophenonetetracarboxylic dianhydride),

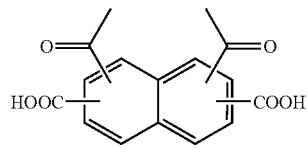

(from 1,4,5,8-naphthalenetetracarboxylic dianhydride, 1,2,5, 6-naphthalenetetracarboxylic dianhydride or 2,3,6,7-naphthalenetetracarboxylic dianhydride, wherein a carbonyl group and a carboxyl group may be substituted on any carbon position except for a linking portion of the rings),

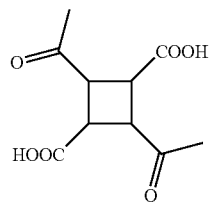

(from cyclobutanetetracarboxylic dianhydride),

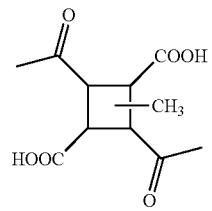

(from methylcyclobutanetetracarboxylic dianhydride), or

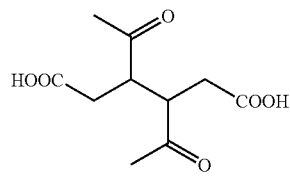

(1,2,3,4-tetracarboxybutane dianhydride), where the moiety A is a group generated by a reaction between an amino group of $NH_2(CH_2)_nNH_2$ where n is an integer from 1 to 10 and the corresponding tetracarboxylic acid anhydride (specified in parentheses).

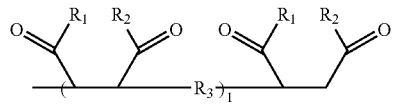

where $R_1$ and $R_2$ are each independently selected from the group consisting of an —OH group and an —$NH_2(CH_2)_nNH_2$ group, where n is an integer from 1 to 10; $R_3$ is an alkyl group having 1 to 10 carbon atoms; and l is an integer from 1 to 30,000.

The compounds of Formula 7 and Formula 8 may be the compounds of Formula 9 and Formula 10 below, respectively.

(9)

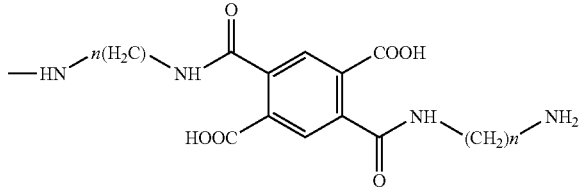

where n is an integer from 1 to 10.

(10)

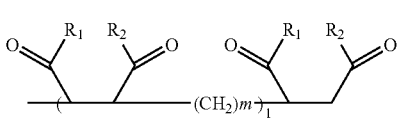

where $R_1$ and $R_2$ are each independently selected from the group consisting of an —OH group and an —$NH(CH_2)_nNH_2$ group, where n is an integer from 1 to 10; m is an integer from 1 to 10; and l is an integer from 1 to 30,000.

The group of Formula 10 may contain a positive charge to negative charge ratio of about 2:1 at a first pH. More preferably, the group of Formula 10 contains the —OH group and the —$NH(CH_2)_nNH_2$ group at a ratio of about 2:1. An example of the group of Formula 10 is a group in which the —$NH(CH_2)_nNH_2$ group is ethylenediamine.

In the present embodiment, the solid substrate may be made of silicone, glass or plastic, but is not limited thereto. The solid substrate may also be activated for immobilization of the group represented by Formula 9 or Formula 10. For example, the solid substrate can be a substrate coated with an active group such as an amino group.

According to an embodiment of the present invention, a solid phase material in which the group of Formula 9 or Formula 10 is immobilized on a solid substrate can be prepared by any of the methods known in the art. For example, the solid phase material can be prepared by immobilizing 1,2,4,5-benzenetetracarboxylic anhydride on a solid substrate (for example, silicone, glass or plastic) coated with an amino group such as $NH_2(CH_2)_nNH_2$ through a chemical reaction, and then chemically reacting the resulting product with $NH_2(CH_2)_nNH_2$, where n is an integer from 1 to 10 (for example, ethylenediamine). In addition, a solid phase material on which the functional group of Formula 10 is immobilized can be prepared, for example, by immobilizing a polyanhydride of Formula 5 on a solid substrate coated with an amino group through a chemical reaction, and then chemically reacting the resulting product with $NH_2(CH_2)_nNH_2$, where n is an integer from 1 to 10 (for example, ethylenediamine).

The first pH may be lower than the pKa value of the carboxyl group in the compound of Formula 1 or 2, or that in the group of Formula 3 or 4. Specifically, the first pH value may be from 2 to 3.5, but it is not limited to these values.

The method includes a process of separating nucleic acid from the above-obtained material-nucleic acid complex at a second pH which is higher than the first pH. The process of separating nucleic acid comprises a process of separating the above-described nucleic acid-bifunctional material complex from the mixture and eluting the nucleic acid-bifunctional material complex in a solution at the second pH.

The second pH can be any value, as long as it is greater than the first pH, and it may be between 5 and 10. The solution used for eluting the nucleic acid-bifunctional material complex may be water, a buffer solution or the like.

The present invention will now be described with reference to the following examples, which are for illustrative purposes only, and not intended to limit the scope of the present invention.

EXAMPLES

Example 1

In Example 1, a substrate having a group of Formula 3, with n being 2, immobilized thereon was prepared, and the amount of DNA bound thereto according to pH was measured.

First, glass substrates coated with an amino group (Corning GAPS glass by Corning Inc.) were immersed in a 100 mM 1,2,4,5-benzenetetracarboxylic anhydride solution in N-methyl-2-pyrrolidone (NMP) for 1 hour, subsequently washed with acetone, and dried in a vacuum. The obtained glass substrates, covalently bonded with 1,2,4,5-benzenecarboxylic anhydride, were immersed in a 100 mM ethylenediamine solution in N-methyl-2-pyrrolidone (NMP) for 1 hour, and then washed with ethanol to obtain glass substrates coated with the group of Formula 3, with n being 2.

The glass substrates were subjected to a reaction with DNA having SEQ ID No:1, which was labeled with Cy3 at the 5'-terminal, at various pH values (3, 7 and 10). The reaction was carried out by coating a solution containing 1 μM of the DNA on the substrates, enclosing the substrates and leaving the substrates to stand at room temperature for 30 minutes. A 0.15 M sodium acetate buffer, a 0.15 M Tris buffer and a 0.15 M sodium carbonate buffer were used for pH 3, 7 and 10, respectively. The results were obtained by washing the substrates with the 0.15 M sodium acetate buffer, the 0.15 M Tris buffer and the 0.15 M sodium carbonate buffer, respectively, and then measuring the amounts of bound DNA with a GenePix scanner (Molecular Devices Corp., USA) at 532 nm (PMT 300). FIG. 1 is a diagram illustrating the results obtained by observing the amounts of DNA bound at pH 3, 7 and 10, respectively. For the control, a glass substrate that was not coated with the functional group of Formula 3 with n being 2, that is, a glass substrate coated with an amino group (Corning GAPS glass, Corning Inc.), was used.

As can be seen from FIG. 1, a large amount of DNA bound to the substrate of the present invention at pH 3, but the binding amounts remarkably decreased at pH 7 and pH 10. This indicates that, with the increase in pH, the charge on the surface changed from positive to negative. The fluorescence intensities observed in FIG. 1 are presented in Table 1 below.

TABLE 1

|  | pH | 3 | 7 | 10 |
|---|---|---|---|---|
| Substrate | Present Invention | 4159 | 32 | 32 |
|  | Control | 6927 | 1648 | 358 |

Example 2

In Example 2, the substrates prepared in Example 1, on which the group of Formula 3, with n being 2, was immobilized, were subjected to DNA binding at pH 3, and then the amounts of DNA released from the nucleic acid-substrate complex were measured at pHs of 3, 5 and 7.

Figure 2:
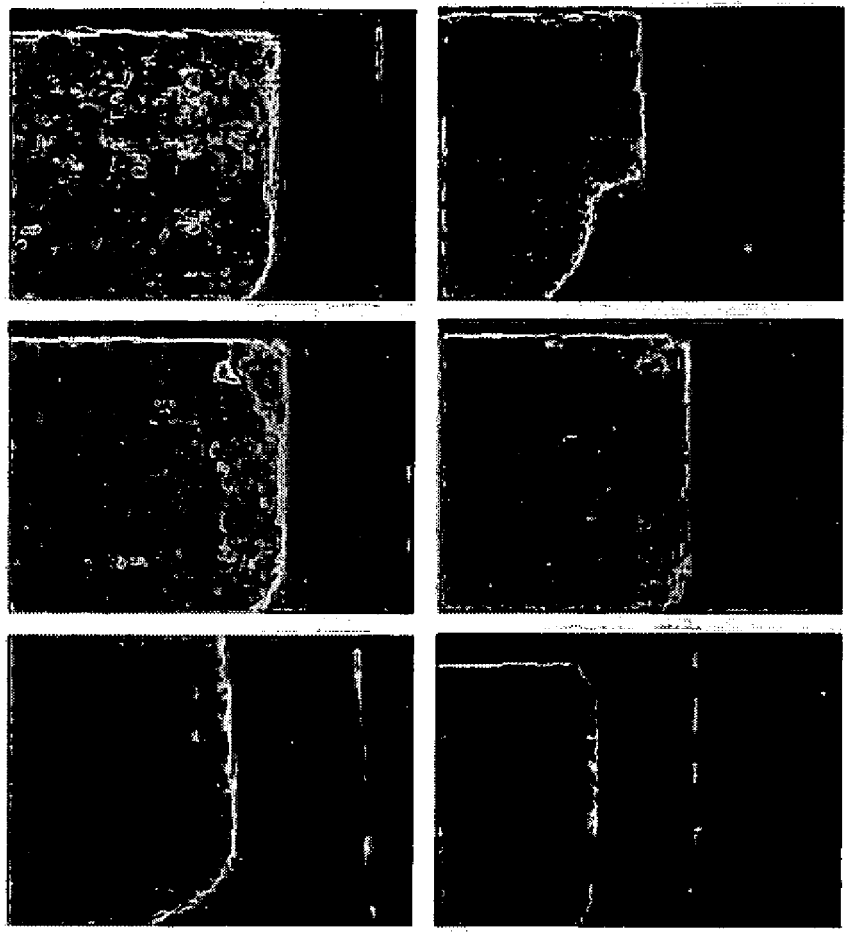
FIG. 2 is a diagram illustrating observations of the amounts of DNA released in accordance with the change in pH.

The resulting glass substrates were subjected to a reaction with DNA having SEQ ID NO:1, which was labeled with Cy3 at the 5'-terminal, at a pH value of 3. The reaction was carried out by coating a solution containing 1 μM of the DNA on the substrates, enclosing the substrates and leaving the substrate to stand at room temperature for 30 minutes. A 0.15 M sodium acetate buffer was used for this. After the reaction, the substrate was washed with a 0.15 M sodium acetate buffer, at various pH values (3, 5 and 7) and then the amounts of bound DNA were measured with a GenePix scanner (Axon Instrument, USA) at 532 nm (PMT 380). For the control, a glass substrate that was not coated with the functional group of Formula 3 with n being 2, that is, a glass substrate coated with an amino group (Corning GAPS glass, Corning Inc.), was used. FIG. 2 is a diagram illustrating observations of the amounts of DNA released in accordance with the change in pH.

As can be seen from FIG. 2, when the pH of the washing solution was increased from pH 3, 80% of the DNA was recovered at pH 7 in the case of the present invention, whereas only 65% of the DNA was recovered in the case of control. Thus, it is obvious that the DNA releasing ability of the substrate of the present invention, that is, the recovery ability, is high, and therefore the efficiency of DNA separation is markedly high. The fluorescence intensities observed in FIG. 2 are presented in Table 2 below.

TABLE 2

|  | pH | 3 | 5 | 7 |
|---|---|---|---|---|
| Substrate | Present Invention | 15147 | 3588 | 2991 |
|  | Control | 37041 | 16458 | 12602 |

Example 3

Recovery of Nucleic Acid Using Substrate with Immobilized Group of Formula 4

In Example 3, a substrate having a group of Formula 4 immobilized thereon was prepared, nucleic acid was bound to the substrate by forming a nucleic acid-material complex at a first pH, and the nucleic acid was recovered from the DNA-substrate complex at a second pH.

In this Example, the following group of Formula 4 was used:

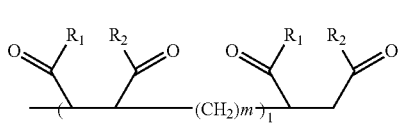

(4)

where $R_1$ and $R_2$ are each independently selected from group consisting of an —OH group and an —NH$(CH_2)_n$NH$_2$ group, wherein n is 2; m is 2; l is 1 to 30,000; and the ratio of the amino group to the carboxyl group of $R_1$ and $R_2$ was adjusted according to the reaction conditions for introduction of NH$_2$(CH$_2$)$_n$NH$_2$.

The functional group of Formula 4 was immobilized on the substrate as follows. First, a glass substrate coated with an amino group (Corning GAPS glass, Corning Inc.) was immersed in a 200 mM (in terms of the molarity of the repeating unit) solution of polyanhydride (Poly(ethylene-alt-maleic anhydride)) (Molecular weight 100,000 to 500,000) in N-methyl-2-pyrrolidone (NMP) for 1 hour, subsequently washed with acetone, and dried in a vacuum. The obtained glass substrates on which the polyanhydride was covalently bonded were immersed in a varing concentration of ethylenediamine solution in N-methyl-2-pyrrolidone (NMP) for 1 hour, and then washed with ethanol and dried. In experimental group 1, the concentration of ethylenediamine was 500 mM; in experimental group 2, the concentrations of ethylenediamine and water were 450 mM and 50 mM, respectively (molar ratio of ethylenediamine/H$_2$O=9:1); in experimental group 3, the concentrations of ethylenediamine and water were 400 mM and 100 mM, respectively (molar ratio of ethylenediamine/H$_2$O=8:2); in experimental group 4, the concentrations of ethylenediamine and water were 300 mM and 200 mM, respectively (molar ratio of ethylenediamine/H$_2$O=6:4); and in experimental group 5, the concentrations of ethylenediamine and water were 200 mM and 300 mM, respectively (molar ratio of ethylenediamine/H$_2$O=4:6).

The resulting glass substrates coated with the group of Formula 4 were subjected to a reaction with DNA having SEQ ID No:1, which was labeled with Cy3 at the 5'-terminal, at pH 3. The reaction was carried out by coating a 0.15 M sodium acetate solution containing 1 µM of the DNA on the substrates, and enclosing and leaving the substrates to stand at room temperature for 5 minutes. After the reaction, the substrates were washed with a 0.15 M sodium acetate buffer at pH 3 and pH 7, respectively, and then the fluorescence intensities were measured with a GenePix scanner (Molecular Devices Corp., USA) at 532 nm (PMT 300). The measured fluorescence intensities are presented in Table 3 below. For the control, a glass substrate that was not coated with the functional group of Formula 4 but with an amino group (Corning GAPS glass, Corning Inc.) was used.

TABLE 3

| Substrate | Fluorescence Intensity | | Recovery (%) |
| --- | --- | --- | --- |
| | pH 3 | pH 7 | |
| Control | 28871 | 7899 | 72 |
| Experimental Group 1 | 42694 | 12369 | 71 |
| Experimental Group 2 | 42453 | 10028 | 76 |
| Experimental Group 3 | 43620 | 10762 | 75 |
| Experimental Group 4 | 43123 | 11143 | 74 |
| Experimental Group 5 | 43398 | 6357 | 85 |

As shown in Table 3, the DNA recovery was highest for experimental group 5, that is, the case where the molar ratio of ethylenediamine/H$_2$O was 4:6.

Example 4

Recovery of Nucleic Acid Using Substrate with Immobilized Group of Formula 4

In Example 4, a substrate having the functional group of Formula 4 coated thereon was used in a reaction with DNA for different reaction times, and then nucleic acid was isolated. The substrate having the functional group of Formula 3 coated thereon was obtained by carrying out a reaction with experimental group 5 of Example 3, where the molar ratio of ethylenediamine/H$_2$O was 4:6.

The glass substrates of experimental group 5 were subjected to a reaction with DNA having SEQ ID No:1, which was labeled with Cy3 at the 5'-terminal, at pH 3 for various reaction times. The reaction was carried out by coating a 0.15 M sodium acetate solution containing 1 µM of the aforementioned DNA on the substrates, and enclosing and leaving the substrate to stand at room temperature for 1, 5, 10 and 30 minutes, respectively. After the reaction, the substrates were washed with a 0.15 M sodium acetate buffer at pH 3 and pH 7, respectively, and then the fluorescence intensities were measured with a GenePix scanner (Molecular Devices Corp., USA) at 532 nm (PMT 350). The measured fluorescence intensities are presented in Table 4 below. For control group 1, a glass substrate that was not coated with the functional group of Formula 3 but with an amino group (Corning GAPS glass, Corning Inc.) was used. For control group 2, the reaction was carried out by coating a Qiagen (QIAquick PCR Purification Kit, Qiagen Co., Ltd.) binding buffer containing 1 µM of the DNA on a glass substrate coated with an amino group (Corning GAPS glass, Corning Inc.) in a piranhas solution (H$_2$O$_2$:H$_2$SO$_4$=1:3), and enclosing and leaving the substrate to stand at room temperature for 30 minutes. After the reaction, the substrates were washed with a Qiagen washing buffer at pH 3 and pH 7, respectively, and the fluorescence intensities were measured with a GenePix scanner (Molecular Devices Corp., USA) at 532 nm (PMT 350).

TABLE 4

| Substrate | Reaction Time (min) | Fluorescence Intensity | | Recovery (%) |
| --- | --- | --- | --- | --- |
| | | pH 3 | pH 7 | |
| Experimental Group 5 | 1 | 39305 | 1844 | 95 |
| | 5 | 38684 | 5398 | 86 |
| | 10 | 36810 | 5111 | 87 |
| | 30 | 44083 | 5495 | 87 |

TABLE 4-continued

| Substrate | Reaction Time (min) | Fluorescence Intensity pH 3 | pH 7 | Recovery (%) |
|---|---|---|---|---|
| Control Group 1 | 1 | 26372 | 7332 | 67 |
| | 5 | 23307 | 8611 | 63 |
| | 10 | 24798 | 8273 | 67 |
| | 30 | 26886 | 12300 | 54 |
| Control Group 2 | 30 | 27189 | 7083 | 74 |

As shown in Table 4, when the substrate of experimental group 5 was used, 95% of the DNA could be recovered within

```
                    SEQUENCE LISTING

<160> NUMBER OF SEQ ID NOS: 1

<210> SEQ ID NO 1
<211> LENGTH: 50
<212> TYPE: DNA
<213> ORGANISM: Artificial Sequence
<220> FEATURE:
<223> OTHER INFORMATION: primer

<400> SEQUENCE: 1
ggcctcactt cctggggtca tgacccagg cctggaggcc tgcttccctt           50
```

1 minute. This indicates that the present invention has a markedly high rate of recovery compared to control group 1 and control group 2.

Example 5

Confirmation of Bound Nucleic Acid by EtBr Staining

In Example 5, the substrate coated with the group of Formula 4 was reacted with bacterial genomic DNA, and then the presence of bound nucleic acid was confirmed by EtBr staining. The substrate having the functional group of Formula 4 thereon was obtained by carrying out a reaction with experimental group 5 of Example 3, where the molar ratio of ethylenediamine/H$_2$O was 4:6.

The glass substrates of experimental group 5 were subjected to a reaction with bacterial genomic DNA (E. coli genomic DNA, extracted using Qiagen DNA Miniprep Kit), which was labeled with Cy3 at the 5'-terminal, for 20 minutes at pH 3 and pH 7, respectively. The reaction was carried out by coating a 0.15 M sodium acetate solution containing 10 ng/µl of the DNA on the substrates, and enclosing and leaving the substrates to stand at room temperature for 20 minutes. After the reaction, the substrates were washed with 0.15 M sodium acetate solutions at pH 3 and pH 7, respectively, and then were immersed in a solution containing EtBr to stain the nucleic acid with EtBr. The stained nucleic acid was confirmed by autoradiography. For the control, a sample containing the same group of Formula 4 but not treated with DNA was used.

Figure 3:
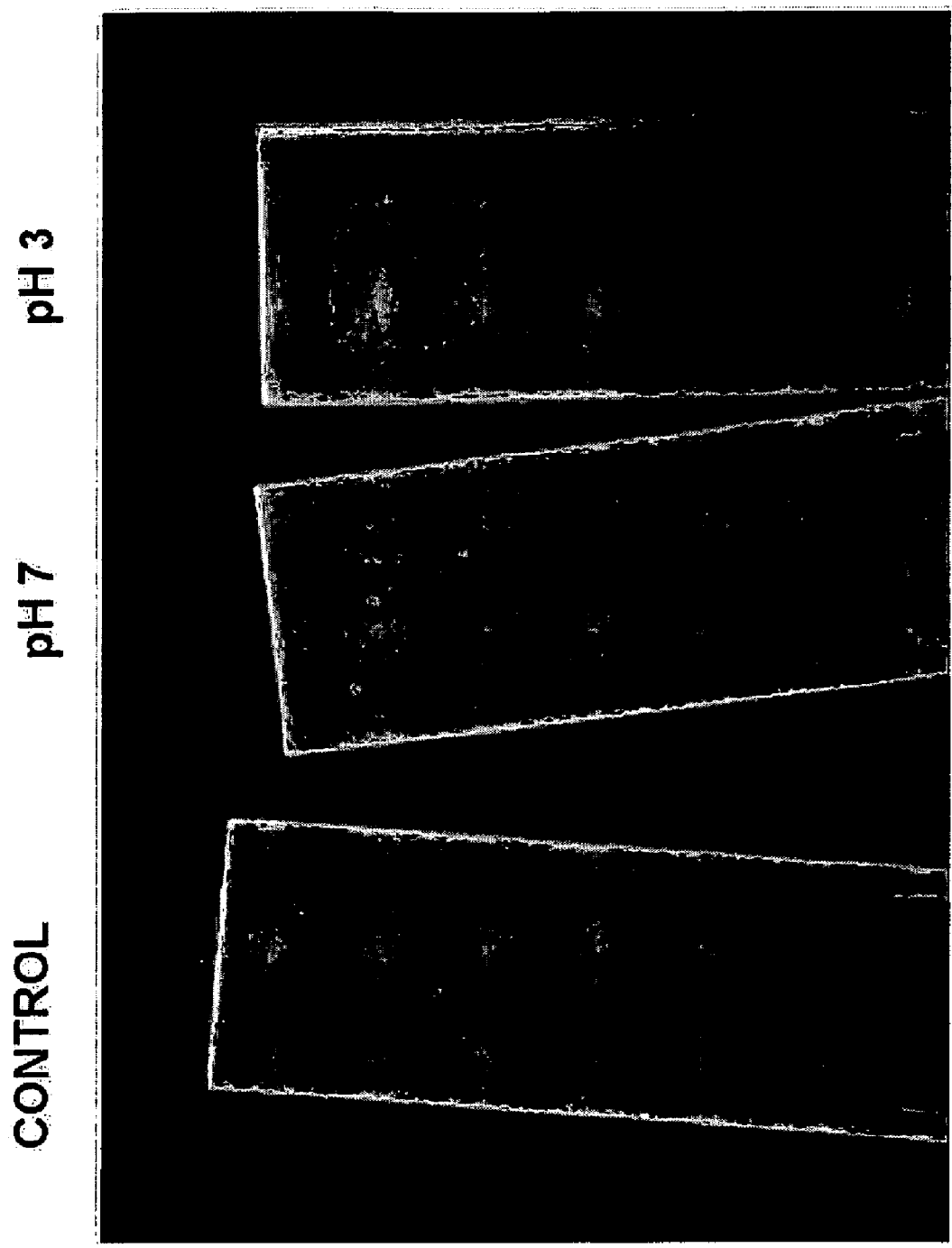
FIG. 3 is a diagram illustrating the results of staining the substrates reacted with bacterial genomes at pH 3 and pH 7, respectively, using EtBr.

FIG. 3 is a diagram illustrating the results of EtBr staining of the substrates subjected to the reaction with bacterial genome at pH 3 and pH 7. As shown in FIG. 3, DNA of long length was purified.

As described above, in a method of isolating nucleic acid according to the present invention, nucleic acid can be isolated more rapidly and more efficiently.

While the present invention has been particularly shown and described with reference to exemplary embodiments thereof, it will be understood by those skilled in the art that various changes in form and details may be made therein without departing from the spirit and scope of the invention as defined by the appended claims.

What is claimed is:

1. A method of isolating nucleic acid from a sample containing nucleic acid, the method comprising:

contacting the sample with a bifunctional material that contains an amino group and a carboxyl group and is positively charged at a first pH to allow binding of nucleic acid to the bifunctional material to form a nucleic acid-bifunctional material complex; and extracting the bound nucleic acid at a second pH which is higher than the first pH from the complex, wherein the bifunctional material is represented by the following Formula 1 or Formula 2:

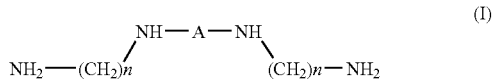

where n is an integer from 1 to 10; and A is

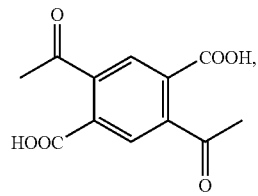

-continued

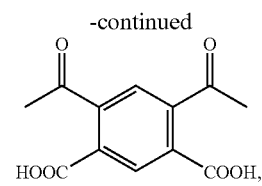

or a combination, from 1,2,4,5-benzenetetracarboxylic dianhydride;

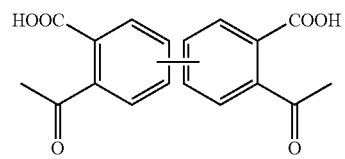

from 3,3',4,4'-biphenyltetracarboxylic dianhydride, 2,2',3,3'-biphenyltetracarboxylic dianhydride, or 2,3,3',4'-biphenyltetracarboxylic dianhydride;

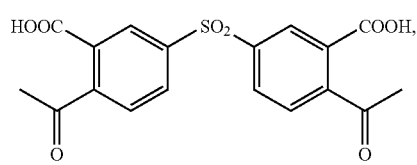

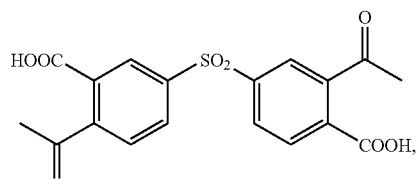

or a combination, from bis(3,4-dicarboxyphenyl)sulfone dianhydride;

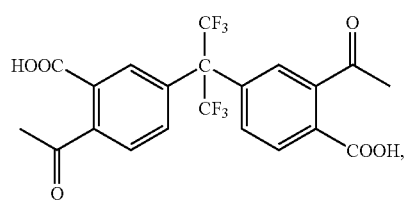

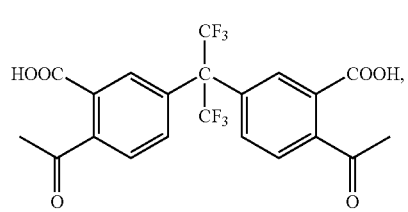

or a combination, from 2,2-bis(3,4-dicarboxyphenyl)-hexafluoropropane dianhydride;

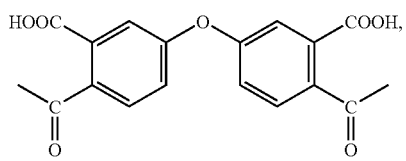

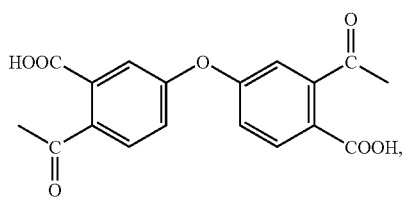

or a combination, from bis(3,4-dicarboxyphenyl) ether dianhydride;

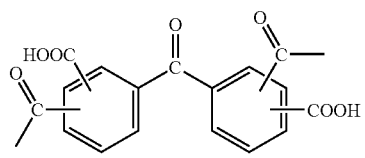

from 3,3',4,4'-benzophenonetetracarboxylic dianhydride, 2,2',3,3'-benzophenonetetracarboxylic dianhydride or 2,3,3',4'-benzophenonetetracarboxylic dianhydride;

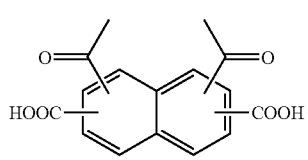

from 1,4,5,8-naphthalenetetracarboxylic dianhydride, 1,2,5,6-naphthalenetetracarboxylic dianhydride, or 2,3,6,7-naphthalenetetracarboxylic dianhydride, wherein the naphthalene is further unsubstituted or a carbonyl group and a carboxyl group is substituted on any carbon position except for a linking portion of the rings;

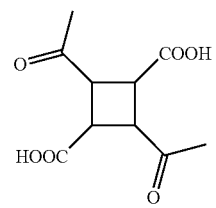

from cyclobutanetetracarboxylic dianhydride;

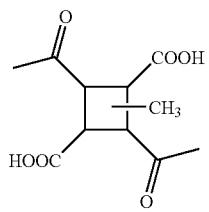

from methylcyclobutanetetracarboxylic dianhydride; or

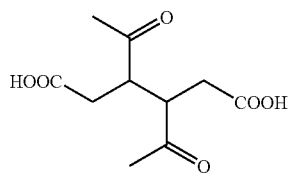

from 1,2,3,4-tetracarboxybutane dianhydride, wherein moiety A is a group generated from a reaction between the corresponding tetracarboxylic dianhydride, and an amino group of an $NH_2(CH_2)_nNH_2$ where n is an integer from 1 to 10; and

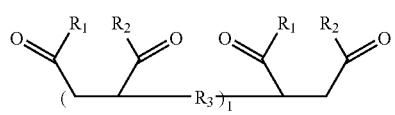
(2)

where $R_1$ and $R_2$ are each independently selected from the group consisting of an —OH group and an —$NH(CH_2)_nNH_2$ group, where n is an integer from 1 to 10; $R_3$ is an alkyl group having 1 to 10 carbon atoms; and 1 is an integer from 1 to 30,000.

2. The method of claim 1, wherein the bifunctional material is represented by Formula 3 or Formula 4 below:

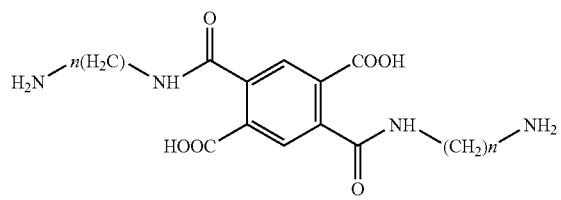
(3)

where n is an integer from 1 to 10; and

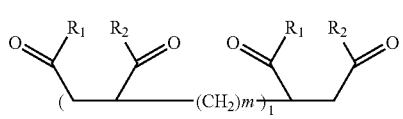
(4)

where $R_1$ and $R_2$ are each independently selected from the group consisting of an —OH group and an —$NH(CH_2)_nNH_2$ group, where n is an integer from 1 to 10; m is an integer from 1 to 10; and 1 is an integer from 1 to 30,000.

3. The method of claim 1, wherein the extracting nucleic acid comprises isolating the nucleic acid-bifunctional material complex from the mixture and eluting the nucleic acid-bifunctional material complex in a solution having the second pH.

4. The method of claim 1, wherein the first pH is in the range of 2 to 3.5, and the second pH is in the range of 5 to 10.

5. The method of claim 2, wherein the compound of Formula 4 contains the —OH group and the —$NH(CH_2)_nNH_2$ group, where n is an integer from 1 to 10 at a ratio of 2:1.

6. The method of claim 1, wherein the bifunctional material is a solid phase material on which a group represented by Formula 9 or Formula 8 below is immobilized:

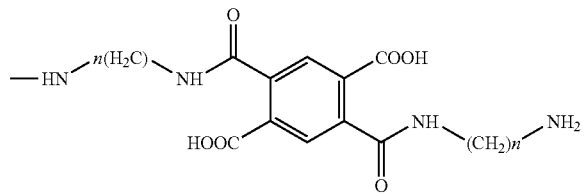
(9)

where n is an integer from 1 to 10; and

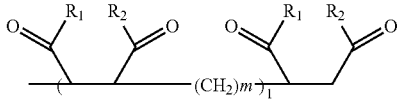
(8)

where $R_1$ and $R_2$ are each independently selected from the group consisting of an —OH group and an —$NH(CH_2)_nNH_2$ group, where n is an integer from 1 to 10; m is an integer from 1 to 10; and 1 is an integer from 1 to 30,000.

7. The method of claim 6, wherein the solid substrate is made of a material selected from the group consisting of silicone, glass and plastic.

8. The method of claim 6, wherein the extracting nucleic acid comprises isolating the nucleic acid-bifunctional material complex from the mixture and eluting the nucleic acid-bifunctional material complex in a solution having the second pH.

9. The method of claim 6, wherein the first pH is in the range of 2 to 3.5, and the second pH is in the range of 5 to 10.

10. The method of claim 6, wherein the compound of Formula 8 contains the —OH group and the —$NH(CH_2)_nNH_2$ group, where n is an integer from 1 to 10 at a ratio of 2:1.

* * * * *